United States Patent
Schörken et al.

(10) Patent No.: US 7,737,289 B2
(45) Date of Patent: Jun. 15, 2010

(54) PROCESS FOR ENRICHING POLYUNSATURATED FATTY ACIDS

(75) Inventors: Ulrich Schörken, Duesseldorf (DE); Peter Kempers, Moenchengladbach (DE); Andreas Sander, Illertissen (DE)

(73) Assignee: Cognis IP Management GmbH, Duesseldorf (DE)

( * ) Notice: Subject to any disclaimer, the term of this patent is extended or adjusted under 35 U.S.C. 154(b) by 0 days.

(21) Appl. No.: 12/060,947

(22) Filed: Apr. 2, 2008

(65) Prior Publication Data

US 2008/0242879 A1    Oct. 2, 2008

(30) Foreign Application Priority Data

Apr. 2, 2007  (EP) .................. 07006847

(51) Int. Cl.
    *C07C 57/00*  (2006.01)
(52) U.S. Cl. .............. 554/227; 554/224; 435/134
(58) Field of Classification Search ............ 554/224, 554/227; 435/134
    See application file for complete search history.

(56) References Cited

U.S. PATENT DOCUMENTS

| 5,897,994 | A | 4/1999 | Sandoz et al. |
| 6,537,787 | B1 | 3/2003 | Breton |

FOREIGN PATENT DOCUMENTS

| EP | 421867 | 4/1991 |
| EP | 0528844 | 10/1991 |
| EP | 0741183 | 11/1996 |
| EP | 06023997 | 11/2006 |
| JP | 03108489 | 5/1991 |
| WO | 91/16443 | 10/1991 |
| WO | 95/24459 | 9/1995 |
| WO | 96/26287 | 8/1996 |
| WO | 96/37586 | 11/1996 |
| WO | 96/37587 | 11/1996 |
| WO | 97/19601 | 6/1997 |
| WO | 00/49117 | 8/2000 |
| WO | 00/73254 | 12/2000 |
| WO | 2004/043894 | 5/2004 |
| WO | 2005/007864 | 1/2005 |
| WO | WO 2005007864 A2 * | 1/2005 |
| WO | 2007/119811 | 10/2007 |

OTHER PUBLICATIONS

Crooks et al., "Comparison of Hydrolysis and Esterification Behavior of *Humicola lanuginosa* and *Rhizomucor miehei* Lipases in AOT-Stabilized Water-in-Oil Microemulsions: I. Effect of pH and Water Content on Reaction Kinetics", Biotechnology and Bioengineering, 1995, vol. 48, pp. 78-88.

Crooks et al., "Comparison of Hydrolysis and Esterification Behavior of *Humicola lanuginosa* and *Rhizomucor miehei* Lipases in AOT-Stabilized Water-in-Oil Microemulsions: II. Effect of Temperature on Reaction Kinetics and General Considerations of Stability and Productivity", Biotechnology and Bioengineering, 1995, vol. 48, pp. 190-196.

European Search Report.

* cited by examiner

*Primary Examiner*—Deborah D Carr

(57) ABSTRACT

A process for enriching and separating polyunsaturated fatty acid (PUFA) acyl groups in a fatty acid mixture, which mixture contains other non-PUFA fatty acid acyl groups, is disclosed.

15 Claims, No Drawings

PROCESS FOR ENRICHING POLYUNSATURATED FATTY ACIDS

CROSS-REFERENCE TO RELATED APPLICATIONS

This application claims priority under 35 U.S.C. Section 119 of European Patent Application No. 07006847.3 filed Apr. 2, 2007, the contents of which are incorporated herein in its entirety.

FIELD OF THE INVENTION

This invention relates to a process for enriching polyunsaturated fatty acid (hereinafter "PUFA") acyl groups in a fatty acid ester mixture which contains PUFA acyl groups and other fatty acid acyl groups, comprising the steps of preparing a fatty acid ester mixture containing PUFA acyl groups and other fatty acid acyl groups, contacting this mixture with a lipase and with water, the water having a pH above 7 and containing a metal salt which forms poorly soluble salts with free fatty acids in water at a pH above 7 and the lipase having a negative selectivity for PUFA acyl groups, so that the other fatty acid acyl groups are hydrolytically split off from the fatty acid ester mixture more rapidly than the PUFA acyl groups, and separating the second fatty acid ester mixture enriched with PUFA acyl groups.

In the context of the present invention, a fatty acid is a saturated or unsaturated, branched or unbranched aliphatic carboxylic acid. Fatty acids can be saturated, mono-unsaturated, di-unsaturated or at least tri-unsaturated.

In the context of the present invention, fatty acids as such are also referred to as free fatty acids. By comparison, the expression "fatty acid acyl group" in the context of the present invention means the single-bonded residue which is obtained by removal of the H atom from the COOH group. Accordingly, fatty acid acyl groups occur, for example, in free fatty acids. They also occur in esters of fatty acids, for example, esters with glycerol, the so-called glycerides.

BACKGROUND OF THE INVENTION

A fatty acid glyceride is an ester of glycerol and one, two, or three fatty acids. If only one OH group of the glycerol is esterified with a fatty acid, the ester is known as a monoglyceride. If two OH groups of the glycerol are each esterified with a fatty acid, the ester is known as a diglyceride. If all three OH groups of the glycerol are each esterified with a fatty acid, the ester is known as a triglyceride.

In the context of the present invention, the initials "PUFA" stand for "polyunsaturated fatty acid", i.e. a fatty acid which is at least tri-unsaturated.

An omega-3-fatty acid is an at least tri-unsaturated fatty acid and is thus a PUFA. An omega-3-fatty acid has a double bond between the third and fourth carbon atoms counting from the methyl end, the methyl C atom being counted as the first C atom. Special omega-3-fatty acids are EPA ((all-Z)-5,8,11,14,17-eicosapentaenoic acid) and DHA ((all-Z)-4,7,10,13,16,19-docosahexaenoic acid).

In the prior art, PUFA glycerides, i.e. glycerides in which PUFA acyl groups make up a large proportion of all the fatty acyl groups present, are produced in particular by one of the following two processes:

(1) transesterification of fish oil to ethyl esters, enrichment of the PUFAs by distillation and re-synthesis to glycerides. The triglyceride synthesis is generally carried out enzymatically.

(2) selective hydrolysis to fish oils to enrich the PUFAs in the glycerides and purification of the PUFA glyceride by distillation. The selective hydrolysis is generally carried out enzymatically.

Process (1), the enzymatic triglyceride synthesis, is described, for example, in EP-A 0 528 844.

Process (2) or the selectivity of lipases for PUFAs in the hydrolysis of glycerides is disclosed in several patent applications, cf. for example WO 97/19601, WO 95/24459, WO 96/37586, WO 96/37587, EP-A 0 741 183, WO 96/26287, WO 00/73254, WO 04/043894, WO 00/49117 and WO 91/16443.

The following is known from the prior art on enzyme selectivities for PUFAs. Most lipases and phospholipases have a negative selectivity for PUFAs by comparison with other fatty acids typically present in vegetable and fish oils. By "negative selectivity" is meant that the lipases hydrolytically split off the other fatty acid groups from glycerides more rapidly than the PUFA acyl groups. Accordingly, the enzymatic enrichment of PUFAs generally proceeds via a modification of the other "non-PUFA" fatty acids. This can be done by esterification, transesterification, or hydrolysis of esters.

Negative selectivities for PUFAs are described, for example, for *Candida* and *Mucor* lipases. Some enzymes, for example, those isolated from cold water fish, have a positive selectivity for PUFAs.

The microfungus *Thermomyces lanugenosus* was formerly known as *Humicola lanuginosa*. For this reason, there are a large number of scientific treatises on lipase from *Thermomyces* under the name of *Humicola*. The lipase from *Thermomyces* is distinguished in particular by an activity optimum in the alkaline pH range and by high stability, even at a pH of 12 to 13. The enzyme is used in detergents. The articles Biotechnology and Bioengineering 48 (1), 1995; pages 78-88 and Biotechnology and Bioengineering 48 (3), 1995; pages 190-196 provide a good overview of the properties of *Thermomyces* lipase.

Lipase from *Thermomyces lanugenosus* is commercially obtainable, for example, as a liquid preparation with the name Lipozym® TL 100 L or Lipolase® 100 L, from Novozymes A/S, Bagsvaerd, Denmark.

The other lipases used in the following Examples are also commercially obtainable. The lipase from *Geotrichum candidum* was self-produced.

In the following, U stands for "unit" and is an indication of the activity of enzymes. 1 U is the reaction of 1 μmol substance per minute under certain, defined reaction conditions.

Determining the activity of lipase from *Thermomyces lanugenosus* is carried out as follows (for Novozymes A/S by the method for Lipozym® and Lipolase®): the release of butyric acid from glycerol tributyrate is determined at 30° C./pH 7. A 0.16 M tributyrin solution is used for this purpose and butyric acid is titrated with NaOH at a constant pH. 1 unit corresponds to the activity which releases 1 μmol butyric acid from tributyrin per minute.

Fish oils consist essentially of triglycerides containing a mixture of saturated, mono- and poly-unsaturated fatty acids, more particularly with a high proportion of 5×- and 6×-unsaturated fatty acids, which may be used as a health-promoting food supplement. Since the highly unsaturated fatty acids in particular are health-promoting, there is an advantage in enriching them. This can be done, for example, by selective removal of the non-highly unsaturated fatty acids from the triglycerides, for example through selective enzymatic hydrolysis with lipases.

TABLE typical fatty acid compositions of various oils
Typical composition of the main constituents of food fats
(1 = dairy fat; 2 = porcine tallow, 3 = bovine tallow,
4 = sunflower oil, 5 = soybean oil, 6 = olive oil,
7 = rapeseed oil, 8 = palm oil, 9 = sardine oil,
10 = tuna oil, 11 = hydrogenated
vegetable oil (sunflower) are described as follows.

| Fatty acid | 1 | 2 | 3 | 4 | 5 | 6 | 7 | 8 | 9 | 10 | 11 |
|---|---|---|---|---|---|---|---|---|---|---|---|
| C4:0 | 3 | | | | | | | | | | |
| C6:0-C10:0 | 5 | | | | | | | | | | |
| C12:0 | 3 | | | | | | | | | | |
| C14:0 | 10 | 3 | 4 | | | | 1 | 1 | 7 | 3 | |
| C16:0 | 33 | 24 | 30 | 4 | 10 | 11 | 4 | 39 | 18 | 21 | <10 |
| C16:1 | 4 | 3 | 3 | | | | | | 10 | 6 | |
| C18:0 | 9 | 8 | 22 | 4 | 4 | 2 | 1 | 5 | 3 | 6 | >90 |
| C18:1 | 26 | 46 | 38 | 23 | 22 | 75 | 59 | 45 | 15 | 19 | |
| C18:2 | 2 | 8 | 3 | 64 | 53 | 9 | 22 | 8 | | 2 | |
| C18:3 | | | 1 | | 8 | | 10 | | | 1 | |
| C20:5 | | | | | | | | | 17 | 7 | |
| C22:6 | | | | | | | | | 9 | 24 | |

Owing to their large number of double bonds, PUFAs are highly temperature- and oxidation-sensitive. Isomers can easily be formed through migration of the double bonds while peroxides and polymers can easily be formed through oxidation. Where polyunsaturated fatty acids are used in food supplements and pharmaceutical products, it is important to avoid such secondary products in the production process. Particularly in the production of highly enriched PUFAs from fish oils, which are particularly interesting, for example, for administration in the form of capsules, a loss of quality of the end product rapidly occurs through thermal enrichment processes.

A typical working-up process known from the prior art is the distillation-based fractionation of, generally, PUFA ethyl esters which are obtained from the fish oils by chemical transesterification. In this process, the PUFA esters are exposed to severe heat stress by—partly—repeated fractionation.

An alternative process is urea fractionation. Although this process does not involve significant heat stress, it is attended by a serious danger in the formation of toxic secondary products which contaminate the PUFAs.

An alternative method to the enrichment of PUFAs is low-temperature enzymatic fractionation. For example, PUFAs can be enriched in the form of their glycerides or their ethyl esters. The enrichment can be carried out by selective hydrolysis, selective synthesis, or selective transesterification.

However, after the selective enzymatic reaction, there remains the problem of separating the various fractions (for example fatty acid and glycerides) which, generally, are completely soluble in one another. The reaction mixtures from the enzymatic enrichment are generally separated by distillation in a second step. This separation also exposes the PUFAs to heat stress with the risk of a loss of quality.

European patent application 06023997 discloses a single-stage process for the production of zinc ricinoleate in which castor oil is hydrolyzed in the presence of suitable enzymes, preferably lipases, and at the same time reacted with zinc oxide in aqueous solution to form zinc ricinoleate.

WO 2005/007864 discloses a process for the production of carboxylic acid salts and, more particularly, a process for the enzymatic hydrolysis of fish oils in alkaline medium in the presence of calcium salts, the calcium salts of the PUFAs present in the fish oils being obtained.

WO 2005/00784 discloses that the most suitable enzyme for the alkaline hydrolysis of esters is lipase from *Thermomyces lanugenosus*. This lipase was specially developed for detergent applications and shows high activity at alkaline pH values. The lipase is capable of producing soaps (i.e. metal salts) from esters in a one-step reaction in the presence of, for example, $Ca(OH)_2$ or $Mg(OH)_2$. The soaps can then be isolated from the reaction solution by filtration.

WO 07/119811 discloses a method for production of a condensed PUFA oil, which comprises performing an alcoholysis reaction of a PUFA-containing oil-and-fat with a lipase in the presence of at least one compound selected from magnesium oxide, magnesium hydroxide, calcium oxide and calcium hydroxide and a small quantity of water and separating a glyceride fraction.

In principle, most enzymes are capable of catalyzing an ester hydrolysis under alkaline conditions, at least for a short time. *Thermomyces* lipase has the best price/performance ratio of all commercially obtainable lipases.

By way of the present invention, it has now also been discovered that *Thermomyces* lipase has a negative selectivity for PUFAs.

The use of alkaline hydrolysis for enriching PUFAs is also not described in the prior art.

BRIEF SUMMARY OF THE INVENTION

The problem to be addressed by the present invention was to provide a process which would enable the PUFA acyl groups present in a mixture of fatty acid glycerides containing PUFA acyl groups to be enriched without exposure to heat stress.

The problem stated above is solved by the following process according to the invention. The present invention relates to a process for enriching PUFA acyl groups in a first fatty acid ester mixture which contains PUFA acyl groups and other fatty acid acyl groups, comprising:
  preparing the first fatty acid ester mixture containing PUFA acyl groups and other fatty acid acyl groups,
  contacting this mixture with a lipase and with water, the water having a pH above 7 and containing a metal salt which forms poorly soluble salts with free fatty acids in water at a pH above 7 and the lipase having a negative selectivity for PUFA acyl groups, so that the other fatty acid acyl groups are hydrolytically split off from the fatty acid ester mixture more rapidly than the PUFA acyl groups to form a second fatty acid ester mixture enriched with PUFA acyl groups, and
  separating the second fatty acid ester mixture enriched with PUFA acyl groups (preferably without a thermal working-up step).

DETAILED DESCRIPTION OF THE INVENTION

The following processes are particular embodiments of the process according to the invention:
  The process according to the invention in which the first fatty acid ester mixture contains fatty acid triglycerides and, optionally, fatty acid diglycerides and, optionally, fatty acid monoglycerides, and is preferably a fish oil.
  The process according to the invention or an already described process which is a particular embodiment of the present invention and in which the lipase is a lipase which is stable at a pH above 7 and which has high activity (at least 10%, preferably at least 30% and, more particularly, at least 50% of the activity it possesses at a pH below 7).

The process according to the invention or an already described process which is a particular embodiment of the present invention and in which the lipase is lipase from *Thermomyces lanugenosus*.

The process according to the invention or an already described process which is a particular embodiment of the present invention and in which the metal salt is calcium hydroxide or magnesium hydroxide, more particularly calcium hydroxide. In this case, the calcium hydroxide or magnesium hydroxide is preferably present for the most part as a solid suspended in the aqueous phase and only a small part of the poorly soluble hydroxide is dissolved in water. Through the precipitation of poorly soluble fatty acid soaps (salts with calcium or magnesium ions), the dissolved calcium hydroxide or magnesium hydroxide is consumed and replaced by dissolution of the suspended calcium hydroxide or magnesium hydroxide.

The process according to the invention or an already described process which is a particular embodiment of the present invention and in which removal of the second fatty acid ester mixture enriched with PUFA acyl groups comprises removing the poorly soluble salts of the free fatty acids by decantation or centrifugation.

The process according to the invention or an already described process which is a particular embodiment of the present invention and in which removal of the second fatty acid ester mixture enriched with PUFA acyl groups comprises extracting the second fatty acid ester mixture enriched with PUFA acyl groups, more particularly with hydrocarbons.

The present invention also relates to the use of a lipase for enriching PUFA acyl groups in a first fatty acid ester mixture containing PUFA acyl groups and other fatty acid acyl groups, the enrichment being carried out by the process according to the invention or by a process which is a particular embodiment of the present invention.

More particularly, a process is provided in which:
the PUFAs are selectively enriched enzymatically by hydrolysis;
the hydrolysis is carried out in alkaline medium so that the non-PUFA-containing fatty acids released precipitate as a soap phase; and
the PUFA-enriched esters can be extracted under moderate conditions.

More particularly, a process has been developed in which the selective hydrolysis is directly carried out in the presence of an extractant, so that the enriched PUFA ester fraction can be directly isolated after the reaction.

Suitable lipases are any lipases which have a negative selectivity for PUFAs. Lipases with a high activity under alkaline reaction conditions are preferred. *Thermomyces lanugenosus* lipase is particularly preferred. The lipase is preferably used in free form.

Suitable PUFA-containing fatty acid ester mixtures are, in particular, fish oils, enriched glycerides, PUFA-containing ethyl esters, and already concentrated PUFA ethyl esters.

The water to oil ratio (w/w) may be freely selected and, more particularly, is in the range from 10:1 to 1:10 (oil=fatty acid ester mixture).

Preferred metal salts are divalent hydroxides, oxides or carbonates. $Ca(OH)_2$ or $Mg(OH)_2$ are particularly preferred.

The quantity of metal salts used, based on the non-PUFA part of the ester, is preferably 0.3 to 1.5 mol divalent salt per mol non-PUFA fatty acid bound in the ester (corresponds stoichiometrically to 0.6 to 3 times the quantity).

The process of the invention is carried out at temperatures which range from 20 to 60° C., and preferably 25 to 45° C.

The process according to the invention is preferably carried out as a batch reaction, preferably in an inert atmosphere at normal pressure.

The extractant may either be directly introduced into the reaction or used for extraction after the hydrolysis step.

Preferred extractants are water-immiscible solvents such as, for example, alkanes, ethers, etc. Iso-octane, octane, heptane and hexane are particularly preferred.

The ratio of extractant to oil phase (w/w) may be 1:1 to 10:1.

Working up may be carried out, for example, by separation, more particularly by sedimentation and decantation, centrifugation, or coalescence separation using a separator.

Other possible working-up methods include removal of the solvent in vacuo at temperatures of <100° C. and preferably <80° C.

The following examples are illustrative of the invention and should not be construed as limiting in any manner whatsoever.

EXAMPLES

Example 1

Screening for Negative Selectivity for PUFAs on the Basis of Mackerel Oil 10 g mackerel oil and 10 g water were introduced into a flask and heated with stirring to 45° C. or 60° C. Various enzymes were then added in a quantity of at most 1% free enzyme (commercial enzyme preparation) or 3% immobilized enzyme, after which the mixtures were incubated with stirring. Samples were taken during the reaction and the conversion was determined by measurement of the acid value. From a conversion of >40% degree of hydrolysis the fatty acid composition of the fatty acids released was analyzed. The content of glyceride-bound omega-3-fatty acids (mainly EPA and DHA present) was calculated from these data. Enzymes which did not achieve a conversion of 40% over a reaction time of 24 h were not further evaluated. The content of omega-3 fatty acids in the starting oil was 37.6%.

TABLE enzyme screening on the basis of mackerel oil

| Enzyme | Form | Temperature | Conversion | Omega-3 in glyceride |
|---|---|---|---|---|
| *Alcaligenes* sp. | Free | 45° C. | 62% | 51% |
| *Aspergillus niger* | Free | 45° C. | <40% | |

TABLE-continued enzyme screening on the basis of mackerel oil

| Enzyme | Form | Temperature | Conversion | Omega-3 in glyceride |
|---|---|---|---|---|
| Candida antarctica A | Free | 45° C. | 44% | 52% |
| Candida antarctica A | Immobilized | 60° C. | <40% | |
| Candida antarctica B | Free | 45° C. | <40% | |
| Candida antarctica B | Immobilized | 60° C. | 43% | 41% |
| Candida cylindracea | Free | 45° C. | 43% | 55% |
| Candida rugosa | Free | 45° C. | 41% | 55% |
| Pseudomonas fluorescens | Free | 45° C. | 45% | 47% |
| Rhizomucor miehei | Immobilized | 60° C. | <40% | |
| Rhizopus oryzae | Free | 45° C. | 43% | 43% |
| Rhizopus niveus | Free | 45° C. | <40% | |
| Thermomyces lanugenosus | Free | 45° C. | 61% | 48% |
| Thermomyces lanugenosus | Immobilized | 45° C. | 60% | 51% |

Coupled with good hydrolysis activity, the lipases from the organism *Candida* (except for lipase B from *Candida antarctica*) and *Alcaligenes* above all showed good negative selectivity for PUFAs. *Thermomyces lanugenosus* lipase both in free and in immobilized form also showed good selectivity and, at the same time, a good hydrolysis rate. All the enzymes tested showed slight negative selectivity for PUFAs.

Example 2

Screening for Negative Selectivity for PUFAs on the Basis of Menhaden Oil 10 g menhaden oil and 10 g water were introduced into a flask and heated with stirring to 45° C. or 60° C. Various enzymes were then added in a quantity of at most 1% free enzyme (commercial enzyme preparation) or 3% immobilized enzyme, after which the mixtures were incubated with stirring. Samples were taken during the reaction and the conversion was determined by measurement of the acid value. From a conversion of >40% degree of hydrolysis, the fatty acid composition of the fatty acids released was analyzed. The content of glyceride-bound omega-3-fatty acids (mainly EPA and DHA present) was calculated from these data. Enzymes which did not achieve a conversion of 40% over a reaction time of 24 h were not further evaluated. The content of omega-3 fatty acids in the starting oil was 38.0%.

TABLE enzyme screening on the basis of menhaden oil

| Enzyme | Form | Temperature | Conversion | Omega-3 in glyceride |
|---|---|---|---|---|
| Alcaligenes sp. | Free | 45° C. | 58% | 53% |
| Aspergillus niger | Free | 45° C. | <40% | |
| Candida antarctica A | Free | 45° C. | 52% | 59% |
| Candida antarctica A | Immobilized | 60° C. | <47% | 56% |
| Candida antarctica B | Free | 45° C. | <40% | |
| Candida antarctica B | Immobilized | 60° C. | 43% | 45% |
| Candida cylindracea | Free | 45° C. | 49% | 61% |
| Candida rugosa | Free | 45° C. | <40% | |
| Pseudomonas fluorescens | Free | 45° C. | 47% | 49% |
| Rhizomucor miehei | Immobilized | 60° C. | <40% | |
| Rhizopus oryzae | Free | 45° C. | <40% | |
| Rhizopus niveus | Free | 45° C. | <40% | |
| Thermomyces lanugenosus | Free | 45° C. | 41% | 49% |
| Thermomyces lanugenosus | Immobilized | 45° C. | 42% | 50% |

Coupled with good hydrolysis activity, the lipases from the organism *Candida* (except for lipase B from *Candida antarctica*) and *Alcaligenes* above all showed good negative selectivity for PUFAs. *Thermomyces lanugenosus* lipase both in free and in immobilized form also showed good selectivity and an adequate hydrolysis rate. All the enzymes tested showed slight negative selectivity for PUFAs.

Example 3

Screening for Negative Selectivity for PUFAs on the Basis of Tuna Oil 10 g tuna oil and 10 g water were introduced into a flask and heated with stirring to 45° C. or 60° C. Various enzymes were then added in a quantity of at most 1% free enzyme (commercial enzyme preparation) or 3% immobilized enzyme, after which the mixtures were incubated with stirring. Samples were taken during the reaction and the conversion was determined by measurement of the acid value. From a conversion of >40% degree of hydrolysis, the fatty acid composition of the fatty acids released was analyzed. The content of glyceride-bound omega-3-fatty acids (mainly EPA and DHA present) was calculated from these data. Enzymes which did not achieve a conversion of 40% over a reaction time of 24 h were not further evaluated. The content of omega-3 fatty acids in the starting oil was 39.6%.

TABLE enzyme screening on the basis of tuna oil

| Enzyme | Form | Temperature | Conversion | Omega-3 in glyceride |
|---|---|---|---|---|
| Alcaligenes sp. | Free | 45° C. | 58% | 53% |
| Aspergillus niger | Free | 45° C. | <40% | |
| Candida antarctica A | Free | 45° C. | 63% | 64% |
| Candida antarctica A | Immobilized | 60° C. | <40% | |
| Candida antarctica B | Free | 45° C. | <40% | |
| Candida antarctica B | Immobilized | 60° C. | 43% | 46% |
| Candida cylindracea | Free | 45° C. | 53% | 64% |
| Candida rugosa | Free | 45° C. | 41% | 57% |
| Pseudomonas fluorescens | Free | 45° C. | 46% | 50% |
| Rhizomucor miehei | Immobilized | 60° C. | <40% | |
| Rhizopus oryzae | Free | 45° C. | 54% | 49% |
| Rhizopus niveus | Free | 45° C. | <40% | |
| Thermomyces lanugenosus | Free | 45° C. | 61% | 54% |
| Thermomyces lanugenosus | Immobilized | 45° C. | 55% | 48% |

Coupled with good hydrolysis activity, lipases from the organism Candida (except for lipase B from Candida antarctica) above all showed good negative selectivity for PUFAs. Thermomyces lanugenosus lipase both in free and in immobilized form also showed good selectivity and, at the same time, a good hydrolysis rate. All the enzymes tested showed slight negative selectivity for PUFAs. This selectivity is more pronounced with DHA-rich tuna oil than with the EPA-rich fish oils.

Example 4

Enzyme Screening on the Basis of CLA Methyl Ester-Identification of Suitable Lipases and Esterases Batches of 100 mg CLA methyl ester (CLA=conjugated linoleic acid), 0.9 ml water and 15 Mg(OH)$_2$ were each weighed into 16 Eppendorf cups. The reactions were initiated by addition of a lipase or esterase, as listed in the Table. The samples were incubated on a shaker at 30° C. After 5 h, quantities of 3 mg Mg(OH)$_2$ and more lipase were added. The batches were incubated on the laboratory shaker for a total of 24 h at 30° C. After 24 h, the incubation was terminated. The batches were completely frozen without product separation. All batches were freeze-dried, the soaps formed were acid-ligested and the fatty acids released were extracted with iso-octane. After silylation, the fatty acids obtained were analyzed by gas chromatography. The conversions of the enzymatic hydrolases were determined by comparison of the peak areas of the free acids formed with mono-, di- and triglycerides still present.

| Batch | Lipase from organism | Quantity | Quantity after 5 h | Mg(OH)$_2$ after 5 h | Conversion |
|---|---|---|---|---|---|
| 1 | Thermomyces | 5 µl | 5 µl | 3 mg | 100% |
| 2 | Candida antarctica B | 10 µl | 10 µl | 3 mg | 27% |
| 3 | Rhizomucor miehei | 10 µl | 10 µl | 3 mg | 98% |
| 4 | Candida antarctica A | 10 µl | 10 µl | 3 mg | 26% |
| 5 | Candida cylindracea | 10 mg | 10 mg | 3 mg | 96% |
| 6 | Rhizopus javanicus | 10 mg | 10 mg | 3 mg | 96% |
| 7 | Porcine pancreas | 10 mg | 10 mg | 3 mg | 67% |
| 8 | Aspergillus niger | 10 mg | 10 mg | 3 mg | 9% |
| 9 | Candida rugosa | 10 mg | 10 mg | 3 mg | 71% |
| 10 | Mucor javanicus | 10 mg | 10 mg | 3 mg | 98% |
| 11 | Pseudomonas fluorescens | 10 mg | 10 mg | 3 mg | 100% |
| 12 | Rhizopus oryzae | 10 mg | 10 mg | 3 mg | 96% |
| 13 | Pseudomonas sp. | 10 mg | 10 mg | 3 mg | 85% |
| 14 | Chromobacterium viscosum | 10 mg | 10 mg | 3 mg | 99% |
| 15 | Fusarium oxysporum | 10 mg | 10 mg | 3 mg | 99% |
| 16 | Penicilium camenberti | 10 mg | 10 mg | 3 mg | 40% |

Result: All lipases showed activity under the alkaline reaction conditions. Most of the lipases tested achieved a degree of hydrolysis of >80%. Thermomyces lanugenosus lipase showed a particularly good activity/cost profile.

Example 5

Enzyme Screening for the Synthesis of Zinc Ricinoleate from Castor Oil

Batches of 10 g castor oil, 1.35 g zinc oxide and 50 g water were each weighed into 14 closable vessels. Various enzymes (see Table below) were added to the batches. The batches were incubated for 24 h at 30° C. in a shaking incubator. After termination of the reaction, a sample of the zinc ricinoleate formed was taken and the water phase was removed by centrifuging. The samples were analyzed by gas chromatography for their content of zinc soaps and glycerides. To this end, 20 mg of the zinc ricinoleate samples were incubated for 30 mins. at 80° C. with 1 ml BSTFA/MSTFA [6:1] mixture and then analyzed in a DB5 HT column. The results were evaluated via the peak area. Zinc soaps were analyzed in the form of the free acids. The content of ricinoleic acid in the castor oil used and hence in the zinc soaps formed amounted to about 88%. The zinc soaps are referred to simply as zinc ricinoleate in the following.

| Batch | Enzyme (% by wt. based on castor oil) | Manufacturer | Organism |
|---|---|---|---|
| 1 | 1% Lipolase | Novozymes | *Thermomyces lanugenosus* |
| 2 | 1% Novozym 388 | Novozymes | *Rhizomucor miehei* |
| 3 | 1% Novozym 525 | Novozymes | *Candida antarctica* B |
| 4 | 1% Novozym 868 | Novozymes | *Candida antarctica* A |
| 5 | 1% Lipase A | Amano | *Aspergillus niger* |
| 6 | 1% Lipomod 34 | Biocatalysts | *Candida cylindracea* |
| 7 | 1% Lipopan | Novozymes | *Fusarium oxysporum* |
| 8 | 0.5% Lipase GC | Amano | *Geotrichum candidum* |
| 9 | 1% Lipase M | Amano | *Mucor javanicus* |
| 10 | 1% Lipase R | Amano | *Penicilium roquefortii* |
| 11 | 1% Lipase L115P | Biocatalysts | *Porcine Pancreas* |
| 12 | 1% Lipase PS | Amano | *Pseudomonas* sp. |
| 13 | 1% Lipomod 36 | Biocatalysts | *Rhizopus javanicus* |
| 14 | 1% Lipase F-AP 15 | Amano | *Rhizopus oryzae* |

| Batch | Zinc ricinoleate | Monoglyceride | Diglyceride | Triglyceride |
|---|---|---|---|---|
| 1 | 78.1% | 7.8% | 14.1% | 0% |
| 2 | 63.8% | 28.8% | 7.4% | 0% |
| 3 | 15.1% | 0.5% | 5.0% | 79.4% |
| 4 | 6.5% | 0% | 10.5% | 83.0% |
| 5 | 6.8% | 0% | 7.2% | 86.0% |
| 6 | 88.0% | 0% | 12.0% | 0% |
| 7 | 58.7% | 33.3% | 8% | 0% |
| 8 | 93.2% | 0% | 6.8% | 0% |
| 9 | 60.4% | 27.5% | 12.1% | 0% |
| 10 | 37.5% | 13.8% | 47.6% | 1.3% |
| 11 | 18.2% | 0% | 0% | 81.8% |
| 12 | 5.6% | 0% | 8.3% | 86.1% |
| 13 | 92.1% | 0% | 2.0% | 5.9% |
| 14 | 90.4% | 0% | 4.4% | 9.6% |

Result: Where castor oil was used, all the lipases tested showed a hydrolytic reaction under alkaline conditions through the presence of ZnO in the reaction mixture. From the above screening, lipases/esterases or phospholipases from *Thermomyces, Rhizomucor, Candida cylindracea* or *rugosa, Fusarium, Geotrichum, Mucor* and *Rhizopus* are particularly suitable for a one-step hydrolysis coupled with zinc soap formation. The list of hydrolases tested is by no means complete.

Example 6

Screening for Alkaline Enrichment of Concentrated PUFA Ethyl Esters

Batches of 1 g PUFA ethyl ester, 2 g iso-octane, 1 g water and 40 mg $Ca(OH)_2$ were introduced into 10 stirred and closable vessels and stirred. The PUFA ethyl ester used had a total content of 69% eicosapentaenoic and docosahexaenoic acid. Quantities of 50 mg various commercial enzyme preparations from various organisms, as listed in the Table, were added to the batches. The batches were incubated with stirring for 24 h. After 5 h and 24 h, samples were taken and the iso-octane phase was separated by centrifuging from the aqueous phase and the solid phase consisting of calcium soaps. The iso-octane phase contained the unreacted ethyl esters which were analyzed by gas chromatography.

TABLE enrichment of PUFA ethyl esters

| Batch | Lipase | EPA + DHA after 5 h | EPA + DHA after 24 h |
|---|---|---|---|
| 1 | *Thermomyces lanugenosus* | 78.9% | 77.4% |
| 2 | *Rhizomucor miehei* | 65.9% | 67.1% |
| 3 | *Candida cylindracea* | 68.1% | 66.8% |
| 4 | *Rhizopus javanicus* | 68.6 | 67.2% |
| 5 | *Porcine pancreas* | 67.8% | 65.3% |
| 6 | *Candida rugosa* | 68% | 67.2% |
| 7 | *Mucor javanicus* | 67.2% | 66.4% |
| 8 | *Pseudomonas fluorescens* | 68.9% | 67.7% |
| 9 | *Rhizopus oryzae* | 67.1% | 65.9% |
| 10 | *Fusarium oxysporum* | 68.6% | 67.1% |

Result: Under the reaction conditions selected, only *Thermomyces* lipase is capable of further enriching an already-enriched PUFA ethyl ester.

Example 7

Alkaline Enrichment of Concentrated PUFA Ethyl Esters with *Thermomyces* Lipase

Batches of 5 g of the enriched PUFA ethyl ester from Example 6, 10 g iso-octane and 0.1 g $Ca(OH)_2$ were each introduced into 2 reaction vessels. 1 g water was added to batch 1 and 5 g water to batch 2. The reaction was initiated by addition of 100 µl *Thermomyces lanugenosus* lipase (Lipozym TL 100, Novozymes). The batches were incubated with stirring for 48 h at room temperature. After 24 h and 48 h, samples were taken and the iso-octane phase was separated by centrifuging from the aqueous phase and the solid phase consisting of calcium soaps. The iso-octane phase contained the unreacted ethyl esters which were analyzed by gas chromatography.

TABLE enrichment of PUFA ethyl esters with *Thermomyces lanugenosus* lipase

| Batch | EPA + DHA after 24 h | EPA + DHA after 48 h |
|---|---|---|
| 1 | 72.5% | 78.9% |
| 2 | 72.5% | 76.9% |

Result: Good enrichment of the PUFA ethyl ester was achieved irrespective of the quantity of water added.

Example 8

Alkaline Enrichment of PUFA Ethyl Esters with *Thermomyces* Lipase

Batches of 20 g of a PUFA ethyl ester with a total content of 36.8% eicosapentaenoic acid and docosahexaenoic acid and 1.4 g $Ca(OH)_2$ were each introduced into 5 reaction vessels. Iso-octane and water were added to the batches in variable quantities, as listed in the Table. The reaction was initiated by addition of 200 µl *Thermomyces lanugenosus* lipase (Lipozym TL 100, Novozymes). The batches were incubated with stirring for 48 h at room temperature. After 5 h, 24 h and 48 h, samples were taken and the iso-octane phase was separated by centrifuging from the aqueous phase and the solid phase consisting of calcium soaps. The iso-octane phase contained the unreacted ethyl esters which were analyzed by gas chromatography.

TABLE enrichment of PUFA ethyl ester with *Thermomyces lanugenosa* lipase

| Batch | Iso-octane | Water | EPA + DHA after 5 h | EPA + DHA after 24 h | EPA + DHA after 48 h |
|-------|------------|-------|---------------------|----------------------|----------------------|
| 1 | 40 g | 2 g | 44.3% | 54.3% | 60.2% |
| 2 | 40 g | 20 g | 50.1% | 63.6% | 64.1% |
| 3 | 40 g | 80 g | 49.4% | 64.9% | 63.4% |
| 4 | 80 g | 2 g | 43.8% | 45.7% | 51.9% |
| 5 | 80 g | 20 g | 48.3% | 65.2% | 66.8% |

Result: A distinct enrichment of the PUFAs (EPA+DHA) in the ethyl ester phase was achieved in all batches. An increase in the water content in the hydrolysis mixture produced an increase in the hydrolysis rate and hence an improved enrichment per reaction time.

Example 9

Alkaline Enrichment of PUFA Ethyl Ester with *Thermomyces* Lipase 20 g of the PUFA ethyl ester from Example 8, 1.4 g $Ca(OH)_2$ and 60 g water were introduced into a reaction vessel. The reaction was initiated by addition of 100 μl *Thermomyces lanugenosus* lipase (Lipozym TL 100, Novozymes). After a reaction time of 6 h, the mixture was extracted with 30 g iso-octane. After 30 mins. of extraction, the iso-octane phase was separated by centrifuging from the aqueous phase and the solid phase consisting of calcium soaps. The iso-octane phase contained the unreacted ethyl esters which were analyzed by gas chromatography. The extracted ethyl ester phase contained a total of 59.1% EPA and DHA.

What we claim is:

1. A process for enriching polyunsaturated fatty acid (PUFA) acyl groups in a first fatty acid ester mixture which contains PUFA acyl groups and other fatty acid acyl groups, which process comprises:
    (a) preparing the first fatty acid ester mixture containing PUFA acyl groups and other fatty acid acyl groups;
    (b) contacting the mixture with a lipase and with water, the water having a pH above 7 and containing a metal salt which forms poorly soluble salts with free fatty acids in water at a pH above 7 and the lipase having a negative selectivity for PUFA acyl groups, so that the other fatty acid acyl groups are hydrolytically split off from the fatty acid ester mixture more rapidly than the PUFA acyl groups, which forms a second fatty acid ester mixture enriched with PUFA acyl groups, together with poorly soluble fatty acid salts, and
    (c) separating said second fatty acid ester mixture enriched with PUFA acyl groups,
    wherein said contacting step (b) is limited in order to minimize hydrolysis of PUFA acyl groups.

2. The process of claim 1, wherein the first fatty acid ester mixture contains fatty acid triglycerides and, optionally, fatty acid diglycerides and, optionally, fatty acid monoglycerides.

3. The process of claim 2 wherein the first fatty acid ester mixture is derived from fish oil.

4. The process of claim 1, wherein the lipase is a lipase from *Thermomyces lanugenosus*.

5. The process of claim 1, wherein the metal salt is calcium hydroxide or magnesium hydroxide.

6. The process of claim 5, wherein the metal salt is calcium hydroxide.

7. The process of claim 1 wherein the separation of the second fatty acid ester mixture enriched with PUFA acyl groups is carried out by removing the poorly soluble salts of the free fatty acids.

8. The process of claim 7 wherein the removal of the poorly soluble salts of the free fatty acids is carried out by decantation or centrifugation.

9. A process for enriching polyunsaturated fatty acid (PUFA) acyl groups in a first fatty acid ester mixture which contains PUFA acyl groups and other fatty acid acyl groups, which process comprises:
    (a) preparing the first fatty acid ester mixture containing PUFA acyl groups and other fatty acid acyl groups;
    (b) contacting the mixture with a lipase and with water, the water having a pH above 7 and containing a metal salt which forms poorly soluble salts with free fatty acids in water at a pH above 7 and the lipase having a negative selectivity for PUFA acyl groups, so that the other fatty acid acyl groups are hydrolytically split off from the fatty acid ester mixture more rapidly than the PUFA acyl groups, which forms a second fatty acid ester mixture enriched with PUFA acyl groups, together with poorly soluble fatty acid salts, and
    (c) separating said second fatty acid ester mixture enriched with PUFA acyl groups, by extracting said enriched mixture with a hydrocarbon solvent,
    wherein said contacting step (b) is limited in order to minimize hydrolysis of PUFA acyl groups.

10. The process of claim 9 wherein the hydrocarbon solvent is selected from the group consisting of iso-octane, octane, heptane and hexane.

11. The process of claim 9 wherein the hydrocarbon solvent is present in step (b).

12. The process of claim 1 wherein the PUFA acyl groups are derived from omega-3-fatty acid.

13. The process of claim 12 wherein the PUFA acyl groups are comprised of eicosapentaenoic and docosahexaenoic acids.

14. The process of claim 1 wherein said contacting step (b) is carried out to about 40% to about 60% conversion of said fatty acid ester acyl groups.

15. The process of claim 9 wherein said contacting step (b) is carried out to about 40% to about 60% conversion of said fatty acid ester acyl groups.

* * * * *